(12) United States Patent
Ehrhard et al.

(10) Patent No.: US 6,440,442 B1
(45) Date of Patent: *Aug. 27, 2002

(54) HYDROPHILIC POLYMER BLENDS USED FOR DRY COW THERAPY

(75) Inventors: Joseph Ehrhard, Flemington; Michael Eknoian, Newark; Alfredo Vinci, Lawrenceville, all of NJ (US)

(73) Assignee: Hydromer, Inc., Branchburg, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/706,677

(22) Filed: Nov. 6, 2000

Related U.S. Application Data

(63) Continuation-in-part of application No. 09/106,680, filed on Jun. 29, 1998, now Pat. No. 6,203,812, and a continuation-in-part of application No. 09/557,716, filed on Apr. 25, 2000.

(51) Int. Cl.[7] ............................................. A01N 25/24
(52) U.S. Cl. ................ 424/407; 424/78.03; 424/78.05; 424/78.07; 424/78.24; 424/406; 424/438; 424/484; 424/486; 424/667; 424/672; 523/122; 574/635
(58) Field of Search .................. 523/122; 424/78.03, 424/78.05, 78.07, 78.24, 405, 406, 407, 438, 443, 484, 486; 514/635

(56) References Cited

U.S. PATENT DOCUMENTS

| | | |
|---|---|---|
| 3,728,449 A | 4/1973 | Cantor et al. |
| 3,993,777 A | 11/1976 | Caughman et al. |
| 4,049,830 A | 9/1977 | Pugliese |
| 4,113,854 A | 9/1978 | Andrews et al. |
| 4,199,564 A | 4/1980 | Silver et al. |
| 4,258,056 A | 3/1981 | Lentsch |
| 4,311,709 A | 1/1982 | Dybas et al. |
| 4,376,787 A | 3/1983 | Lentsch et al. |
| 4,446,153 A | 5/1984 | Yang |
| 4,542,012 A | 9/1985 | Dell ............................ 424/28 |
| 4,642,267 A | 2/1987 | Creasy et al. |
| 5,017,369 A | 5/1991 | Marhevka |
| 5,192,536 A | 3/1993 | Huprich |
| 5,413,780 A | 5/1995 | Huprich |
| 5,503,838 A | 4/1996 | Schmidt et al. |
| 5,529,770 A | 6/1996 | McKinzie ................... 424/78.2 |
| 5,641,498 A | 6/1997 | Loosemore |

FOREIGN PATENT DOCUMENTS

| | | |
|---|---|---|
| CA | 1 065 254 | 10/1979 |
| WO | 0 473 026 A1 | 3/1992 |
| WO | WO 98/04136 | 2/1998 |

Primary Examiner—Neil S. Levy
(74) Attorney, Agent, or Firm—Hoffmann & Baron, LLP

(57) ABSTRACT

The present invention provides a mammalian teat dip composition capable of being used during a mammal's dry period comprising a solution of a film-forming polymer blend comprising a first polymer component which is an organic, solvent-soluble, preformed, thermoplastic polyurethane having no reactive isocyanate groups and a second polymer component which is a hydrophilic poly(N-vinyl lactam), said blend capable of withstanding exposure to water without significant loss of said hydrophilic poly(N-vinyl lactam) in an amount sufficient to form a water-resistant film upon topical application to mammalian skin; and wherein said blend comprises from about 10 to about 80 weight percent of said first polymer in combination with said solvent and from about 1 to about 20 weight percent of said second polymer; and at least one antimicrobial agent in an amount sufficient to treat and protect mammalian skin from infection; wherein said composition is capable of being removed by peeling.

20 Claims, No Drawings

HYDROPHILIC POLYMER BLENDS USED FOR DRY COW THERAPY

This application is a continuation-in-part of Ser. No. 09/106,680 filed on Jun. 29, 1998, now U.S. Pat. No. 6,203,812, and a continuation-in-part of Ser. No. 09/557,716 filed on Apr. 25, 2000, pending. The entire disclosures of the aforementioned prior applications are incorporated herein by reference.

BACKGROUND OF THE INVENTION

The effective management and maintenance of large dairy herds and the production of dairy products has been a major agricultural accomplishment. One of the problems in maintaining large herds is the health of the individual animals. One health problem that causes significant economic problems relates to mastitis.

The dairy farmer is faced with two different types of mastitis infections, contagious and environmental. Contagious mastitis is spread during the milking process through contact between the animal and dairy equipment that may carry a source of a mastitis pathogen. Environmental mastitis is caused by contamination of the animal skin by materials from the barnyard environment, fields, barn interior, etc, as the animal moves through its environment. Mastitis-causing pathogens include *E. coli, Streptococcus uberis, klebsiella* and others.

Contagious mastitis is most easily controlled by using germicidal post milking teat dip compositions. Such germicidal dips kill bacteria that are introduced onto the surface of the animal from the milking machines. Environmental mastitis is best treated with a barrier film that protects sensitive tissues from contamination.

More particularly, one class of compositions used in the treatment and prevention of mastitis is formed from aqueous coating systems. These coatings reduce the incidence of infection of the animal through the presence of an active biocide. However, these teat dips are easy to remove. For example, polyvinyl alcohol based teat dips, do not provide adequate water resistance. That is, due to exposure to water, these films wear off in about 3 to 4 hours. Without an adequate barrier film the dairy animal is vulnerable to environmental pathogens which will promote mastitis in the herd.

Another class of coating materials is characterized by the formation of film barriers on the skin surface to prevent contact between vulnerable tissues and the environment. Many antimicrobial materials are incompatible with a variety of these film-forming or polymeric materials. For example, antimicrobials cannot be used efficiently with latex since the antimicrobial eventually precipitates out of the latex. Moreover, latex does not provide a long-lasting coverings to the mammalian skin. Recent product developments provide coatings for teat skin which form film barriers, as well as, contain antimicrobial agents. Such coatings include solubilized liquids, polyvinylpyrrolidone and other vinyl polymers, protein hydrozylate, natural and synthetic gums, water, ethanol, methanol, isopropanol, soluble polymers, unsaturated fatty oils, cellulose derivatives, acrylic polymer lattices, etc.

An essential part of a mastitis control program is dry cow therapy. Dry cow therapy is treatment of a cow during the approximately four to ten-week period immediately preceding the delivery of a calf. This period is also known as the dry period or non-lactating period. Although during the dry period the mammal is not exposed to potential contamination form milking machines, forty to fifty percent of teat infections occur during a mammal's dry period. This high rate of infection occurs since a mammal's immune response is diminished during the dry period. Additionally, the teat is distended during the dry period allowing microbials to penetrate the mammary gland more easily; and without the flushing lactation provides, the likelihood of infection increases. Thus, treating a dairy animal during its dry period would minimize the rate of infection.

Furthermore, there are other advantages of treating cows during their dry period vis-à-vis their lactating period. For example, the udder tissue can be exposed to medication for an extended period of time since the medication does not have to be removed prior to milking time. Additionally, if the health of a cow is restored during its dry period, the cow may not have to be treated during its lactating period, thereby reducing the potential of contamination of the milk supply by medicinal agents.

Dry cow therapies that are standard in the industry include teat dip compositions that contain strong solvents, such as tetrahydrofuran. Such solvents are cytotoxic and cause irritation to skin, eyes and the respiratory tract. The irritation to skin includes symptoms such as redness, itching, rash, cracking and pain. Additionally, tetrahydrofuran is harmful if swallowed or inhaled. Repeated or high exposure to tetrahydrofuran may cause kidney or liver damage and may affect the lungs and central nervous system. Additionally, tetrahydrofuran is an extremely flammable liquid and may form explosive peroxides.

Accordingly, it is one of the purposes of this invention, among others, to provide an antimicrobial and long-lasting barrier film teat dip which uses solvents which are dermatologically-acceptable. In particular, these solvents are non-cytotoxic and nonirritating to mammalian skin.

SUMMARY OF THE INVENTION

The present invention provides mammalian teat dip compositions capable of being used during a mammal's dry period. Upon application to mammalian skin, this composition leaves a long-lasting, water-resistant, residual, elastic film. The composition exhibits barrier and antimicrobial properties against mastitis-causing pathogens, thereby protecting the mammal from environmental pathogens. The composition is capable of being removed by peeling.

The composition includes a solution of a film-forming polymer blend and at least one antimicrobial agent.

The polymer blend consists essentially of two polymer components. One polymer component is an organic, solvent-soluble, preformed, thermoplastic polyurethane which has no reactive isocyanate groups. This polymer, along with the solvent used, makes up from about 10 to about 80 weight percent of the composition. The other polymer component is a hydrophilic poly(N-vinyl lactam). This polymer makes up from about 1 to about 15 weight percent of the composition. This polymer blend is capable of withstanding exposure to water without a significant loss of the hydrophilic poly(N-vinyl lactam).

The polyurethane of the polymer blend can be derived from an aromatic polyisocyanate and a polyether polyol; or from an aliphatic polyisocyanate and a polyether polyol; or from an aromatic polyisocyanate and a polyester polyol; or from an aliphatic polyisocyanate and a polyester polyol.

The poly(N-vinyl lactam) of the polymer blend is a water-soluble polyvinylpyrrolidone homopolymer or a poly (N-vinyl caprolactam) homopolymer.

Examples of antimicrobial agents include iodine, chlorhexidine, bronopol and triclosan. In one formulation the iodine antimicrobial agent can be an aqueous solution of polyvinylpyrrolidone-iodine (PVP-$I_2$). In another formulation the iodine antimicrobial agent can be an aqueous solution of elemental iodine and iodide salts. In yet another formulation the iodine antimicrobial agent can be an aqueous solution of elemental iodine, hydriodic acid, and a surfactant. The surfactant can range widely in its degree of ionization, including no ionization.

The chlorhexidine antimicrobial agent can be an aqueous solution of chlorhexidine salts.

The polymer blend can contain at least one additional compatible polymer component. The additional polymer component can be a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

The composition can also contain water-soluble or water-dispersible skin conditioning agents, such as glycerin; glycols; polyols, such as polyethylene glycol; lanolin; aloe vera and vitamins. The composition can also contain colorants, fragrances and insect repellants. The composition can also contain a thickener such as silica or xanthan gum.

The present invention also provides a method of protecting a mammalian teat from infection, in particular of protecting a mammalian teat during the mammal's dry period. This method includes applying the composition of the present invention to the mammalian teat and evaporating the solvent portion of the composition to form a protective water-resistant film.

The compositions and methods of the present invention provide teat dips which have an increased resistance to premature loss. Thus, when an animal is released into the environment, the composition will be resistant to environmental water. Unlike polyvinyl alcohol-based formulations which wear off in about 3 to 4 hours, the compositions of the present invention impart water resistance up to 3 to 7 days. Moreover, the compositions are dermatologically-acceptable. In particular, the compositions are non-cytotoxic and nonirritating to mammalian skin, unlike teat dip compositions that use solvents such as tetrahydrofuran. These and other advantages of the present invention will be appreciated from the detailed description and examples which are set forth herein. The detailed description and examples enhance the understanding of the invention, but are not intended to limit the scope of the invention.

DETAILED DESCRIPTION

The present invention provides mammalian teat dip compositions which are capable of being used during a mammal's dry period. Upon application to mammalian skin, the composition forms an adherent film on the skin. The films protect the teat from infection by preventing contact between the animal's skin and microorganisms either from the environment or from other animals. This invention also discloses methods of protecting mammalian skin from infection with the compositions of the present invention. The compositions and methods of this invention are preferably used during a mammal's dry period. A mammal's dry period is the period four to ten weeks before the mammal delivers offspring.

The compositions include a solution of a polymer blend and at least one antimicrobial agent.

The polymer blend is present in the compositions in an amount which is sufficient to form a water-resistant, residual, elastic film upon topical application to mammalian skin. The polymer blend comprises two polymer components. One polymer component is an organic, solvent-soluble, preformed, thermoplastic polyurethane that has no reactive isocyanate groups. Along with the solvent, this polymer makes up from about 10 to about 80 weight percent of the composition. A preferred low end of this range is about 20, 30, 40, 50, 60 or 70 weight percent of the composition; and a preferred high end of this range is about 60, 70 or 75 weight percent of the composition. The other polymer component is a hydrophilic poly(N-vinyl lactam). This polymer makes up from about 1 to about 20 weight percent of the composition. A preferred low end of this range is about 2, 3, 4 or 5 weight percent of the composition; and a preferred high end of this range is about 7, 8, 10 or 15 weight percent of the composition.

The polyurethane of the polymer blend can be derived from an aromatic polyisocyanate and a polyether polyol; or from an aliphatic polyisocyanate and a polyether polyol; or from an aromatic polyisocyanate and a polyester polyol; or from an aliphatic polyisocyanate and a polyester polyol.

The poly(N-vinyl lactam) of the polymer blend is a water-soluble polyvinylpyrrolidone homopolymer or a poly(N-vinyl caprolactam) homopolymer.

These blends exhibit properties intermediate those of the polyurethane component and those of the poly(N-vinyl lactam) component. These blends are preferably predominantly made up of the polyurethane component and are relatively hard but still wettable. Blends which are predominantly made up of the hydrophilic poly(N-vinyl lactam) component readily absorb water to become soft and slippery.

Exposure of the compositions of the present invention to water, even for prolonged periods, does not result in any significant loss of the hydrophilic poly(N-vinyl lactam) component, possibly as a result of associative forces with the polyurethane component, chain entanglement, or both. Whatever may, in fact, be the basis for this property, this property contributes to the ability of the composition to remain on dairy animals despite prolonged contact with environmental water. There is no significant loss of the composition up to about seven days. A significant loss of the composition would be a loss whereby the composition would no longer have its protective properties.

Since the polyurethane is a preformed polymer having no reactive isocyanate groups, it is stable in solution for indefinite periods of time. Accordingly, polymer products of the instant invention can be readily formed at the point of application as needed simply by evaporating any solvent(s) with which they may be associated. This versatility makes the instant compositions especially convenient for use as coatings.

The polymer blend may contain at least one additional compatible polymer component. An additional compatible polymer component is one that does not interfere with the barrier properties and non-irritability of the composition. The additional polymer component can be a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

These film-forming compositions are dermatologically-acceptable and when applied to mammalian skin, form an adherent film on the skin which does not cause irritation. The films are flexible (i.e., resist cracking), elastic, fluid-resistant, impermeable to pathogens, non-tacky and long-lived. In particular, the films of this invention are highly water-resistant. They can remain on the mammal for up to seven days despite exposure of the animal to environmental water such as rain, dew, ponds, mud, etc. The composition can be reapplied if it has been removed. Additionally, these films permit facile transmission of moisture vapor.

The compositions of the present invention can be conveniently applied to skin as a solution in a dermatologically-acceptable volatile solvent. Dermatologically-acceptable solvents used in the present invention are noncytotoxic and non-irritating to mammalian skin. Examples of such solvents include ethanol, isopropanol, ethyl lactate, diacetone alcohol, methylene chloride, trichloroethylene, N-methyl pyrrolidone and mono and di-ethylene glycol ethers. Ethanol and isopropanol are the preferred solvents. Other solvents can be added to accelerate drying, reduce solvency toward particular substrates, etc., provided such solvents do not interfere with the purposes of the compositions. That is, these solvents are non-cytotoxic, non-irritating to mammalian skin and do not interfere with the antimicrobial and barrier properties of the composition.

The antimicrobial agent is present in the composition in an amount that is sufficient to protect mammalian skin from infection by typical contagious and environmental mastitis-causing pathogens and/or to treat the mammalian skin. Protecting mammalian skin from infection includes the reduction of the incidence of infection. Treating the mammalian skin includes the reduction of the severity of the inflammation and/or infection of the skin. Accordingly, a sufficient amount of antimicrobial would be an amount that would reduce the incidence of infection or reduce the inflammation and/or infection once it has occurred.

Examples of antimicrobial agents used in the present composition include iodine, chlorhexidine, bronopol and triclosan.

One preferred antimicrobial agent is an aqueous solution of iodine (AST, Inc.). A formulation of this aqueous solution can contain 50% to 98.9% by weight of water, 0.1% to 49% by weight of elemental iodine, and 1% to 49.9% % by weight of iodide salts. Another formulation of this aqueous solution can contain 50% to 97.9% by weight of water, 0.1% to 48% % weight of elemental iodine, 1% to 48.9% by weight of hydriodic acid, and 1% to 48.9% by weight of a surfactant. The surfactant can be cationic, anionic, non-ionic or any combination of these. Iodine can also be added as a powder of polyvinylpyrrolidone-iodine (PVP-$I_2$). The aqueous solution formed from PVP-$I_2$ powder can contain 50% to 80% by weight of water and 20% to 50% % by weight of PVP-$I_2$.

Another preferred antimicrobial agent of the invention is an aqueous solution of chlorhexidine. A formulation of such a solution can contain 50% to 99% water and 0.1% to 50% chlorhexidine salts.

In some embodiments, buffering agents can be utilized in this invention. These agents include the acid form and base salt of an organic or inorganic acid in such a ratio to produce a resultant pH value for the resultant composition of about 4 to about 8. A preferred pH range is from about 5 to about 7. The pH range of the composition is preferably adjusted with sodium bicarbonate.

The composition can be applied to the dairy animal in a variety of ways. The material can be sprayed, brushed, dabbed or flooded onto the susceptible sites. One common application mode is by means of a dip. The composition is placed in a small container with a shape adapted to the teat. The teat is then dipped into the container filled with the composition.

In a preferred embodiment, the viscosity of the composition ranges from about 500–5000 cP. This range in viscosity allows an adequate amount of the composition to remain on the mammalian teat when applied without being overly viscous which would make application difficult by dipping or other methods.

The composition can contain various viscosity enhancers or thickeners. The thickener causes aqueous compositions to cling to the surface skin of the animal and enables the composition to resist waste through excessive dripping. Thus, the composition remains in place until it is dry and the barrier layer is formed. Thickeners that can be used in the present composition include natural gums such as xanthan gum (Keltrol TF, Keltrol) or silica. A silane-treated silica is the preferred thickener.

After the mammalian teats have been coated with the composition of this invention, the resulting coating is permitted to dry to an adherent solid film on the teats. Typically, some of the still liquid coating material flows down to the teat end where a plug-like deposit is formed. This deposit or plug also dries to form an adherent solid. This plug is capable of sealing off the teat canal.

The composition can also contain water-soluble or water-dispersible skin conditioning or moisturizing agents that do not degrade barrier properties. The preferred range of these agents in the composition is 0.05% to 10%. Examples of these ingredients are glycerin; glycols; polyols, such as polyethylene glycol; lanolin; aloe vera and vitamins, such as E, C and A. These agents serve to assist in soothing and retaining moisture on the skin.

Agents such as colorants, fragrances and insect repellants (e.g., citronella) may also be included in the composition.

EXAMPLES

The following Examples are intended to show the practice of the invention and are not intended to restrict the scope of the present invention. All percentages are in weight/volume unless otherwise indicated.

Example 1

In a preferred embodiment, the composition of the present invention contains a solution of aliphatic polyurethane resin dissolved in about 50% ethyl alcohol. This solution is about 10 to about 80% of the total weight of the composition. The composition also contains a poly(N-vinyl lactam) in the amount by weight of about 1% to about 15% of the total weight of the composition. The composition includes an effective amount of broad spectrum antimicrobial agent. A silane-treated silica is added to the composition to raise the viscosity and to improve the water resistance of the film in the amount by weight of about 0.5% to about 3% of the total weight of the composition.

Example 2

Persistency Trial:

The teats of four cows (i.e., sixteen quarters) were dipped with the composition of the present invention during their dry period to form a coating on the quarters. The teats were sanitized prior to dipping with a pre-dip containing 0.5% iodine and dried with cloth towel.

The cows were sent out into the environment. Each quarter was evaluated every 12 hours for teat end coverage. The following Table summarizes the results. The second column indicates the number of quarters which show coating loss after a certain period of time. The third column shows the percentage of the coating that was lost on the quarter that was identified as having coating loss.

| Time (hours) | # of Quarters with Coating Loss | % of Coating Lost |
| --- | --- | --- |
| 12–24 | 0 | 0 |
| 24–36 | 1 | 6 |
| 36–48 | 5 | 31 |
| 48–60 | 2 | 13 |
| 60–72 | 4 | 25 |
| over 72 | 4 | 25 |

The results of this experiment show that the composition of the present invention remained on the teats of cows for an extended period of time while the cows were exposed to environmental water.

Example 3

Agar Overlay Cytotoxicity Assay:

An Agar Overlay Cytotoxicity Assay was performed on a sample of the compositions of the present invention. The sample did not induce cytotoxicity after twenty-four hours. In particular, the twenty-four hour reactivity grade was zero versus a positive control of 4.

Accordingly, the results of this experiment show that the compositions of the present invention are non-cytotoxic.

Example 4

Irritancy Test

An evaluation of the dermal irritancy of the composition of the present invention was performed. The test system used albino rabbits by the model suggested in the Annual book ASTM Standard (Volume 13.01) and the CFR (Volume 50, number 188, Rules and Regulation) for evaluating dermal irritancy of test substances. A description of the test system follows.

Three (3) healthy New Zealand white rabbits were used to evaluate the composition of the present invention. The composition was placed on patches that were applied to intact and abraded skin of the rabbits. Adjacent areas of untreated skin of each animal served as a control. After 24 hours, the patches were removed and the rabbits were examined for signs of erythema and edema one hour after patch removal; and at 24, 48, and 72 hours after patch removal.

The skin of the rabbits exposed to the composition of the present invention exhibited a 0.13 Primary Irritation Index. Such a score evinces very low skin irritation. Accordingly, the results of this experiment show that the composition of the present invention are non-irritating to mammalian skin.

Example 5

In one embodiment, the composition of the present invention can be prepared in the following manner. Approximately ten grams of Polyvinyl Pyrrolidone K 90 was added to a 70 gram solution of ethyl alcohol and aliphatic polyurethane with about 31% solids. Once dissolved, approximately 1.5 grams of silica powder (CARB-O-SIL), a silane-treated silica, was dispersed in the solution with a high shear mixer. Next 0.2 grams of Triclosan and 0.5 grams of Food grade Blue dye was dissolved into the solution. The solution was then brought to 100% with the addition of 18.1 grams of Ethanol.

We claim:

1. A mammalian teat dip composition capable of being used during a mammal's dry period comprising:
    (i) a solution of a film-forming polymer blend comprising a first polymer component which is an organic, solvent-soluble, preformed, thermoplastic polyurethane having no reactive isocyanate groups and a second polymer component which is a hydrophilic poly(N-vinyl lactam), said blend capable of withstanding exposure to water without significant loss of said hydrophilic poly(N-vinyl lactam) in an amount sufficient to form a water-resistant film upon topical application to mammalian skin; and wherein said composition comprises from about 10 to about 80 weight percent of said first polymer in combination with a dermatologically-acceptable solvent, and from about 1 to about 15 weight percent of said second polymer;
    (ii) at least one antimicrobial agent in an amount sufficient to treat and protect mammalian skin from infection; and
    (iii) a buffering agent in an amount to provide said composition with a pH of about 4 to about 8;
wherein said composition is capable of being removed by peeling, and wherein said composition is capable of being used during a mammal's dry period.

2. A composition according to claim 1 wherein said antimicrobial agent is selected from the group consisting of iodine, chlorhexidine, bronopol and triclosan.

3. A composition according to claim 1 wherein said antimicrobial agent is an aqueous solution of iodine which comprises polyvinylpyrrolidone-iodine; or elemental iodine and iodide salts; or elemental iodine, hydriodic acid, and a surfactant.

4. A composition according to claim 1 wherein said antimicrobial agent is an aqueous solution of chlorhexidine which comprises 50% to 99% by weight of water and 1.0 to 50% by weight of chlorhexidine salts.

5. A composition according to claim 1 wherein said polyurethane is derived from an aromatic polyisocyanate and a polyether polyol; or is derived from an aliphatic polyisocyanate and a polyether polyol; or is derived from an aromatic polyisocyanate and a polyester polyol; or is derived from an aliphatic polyisocyanate and a polyester polyol.

6. A composition according to claim 1 wherein the poly(N-vinyl lactam) is a water-soluble polyvinylpyrrolidone homopolymer; or is a poly(N-vinyl caprolactam) homopolymer.

7. A composition according claim 1 containing at least one additional polymer component which is compatible therewith, wherein said additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

8. The composition according to claim 1 further including at least one agent selected from the group consisting of skin condition agents, colorants, fragrances, insect repellants and thickeners.

9. A method of protecting mammalian teat from infection during the mammal's dry period comprising:
    (i) applying to mammalian teat a composition comprising a solution of a film-forming polymer blend comprising a first polymer component which is an organic, solvent-soluble, preformed, thermoplastic polyurethane having no reactive isocyanate groups; a second polymer component which is a hydrophilic poly(N-vinyl lactam), said blend capable of withstanding exposure to water without significant loss of said hydrophilic poly(N-vinyl lactam), in an amount sufficient to form a water-resistant film upon application to mammalian skin; a dermatologically-acceptable, volatile solvent; an antimicrobial agent in an amount sufficient to treat and protect mammalian skin from infection; and a buffering agent in an amount to provide said composition with a pH of about 4 to about 8; wherein said composition comprises from about 10 to about 80 weight percent of said first polymer in combination with said solvent, and from about 1 to about 15 weight percent of said second polymer; and (ii) evaporating solvent of said solution whereby a protective water resistant film is formed on said mammalian teat;

wherein said film is capable of forming an elastic film on said mammalian skin during said mammal's dry period.

10. A method according to claim 9 wherein said solvent is selected from the group consisting of ethyl lactate, diacetone alcohol, methylene chloride, trichloroethylene, N-methyl pyrrolidone and mono and di-ethylene glycol ethers, ethanol, propanol, isopropanol, propylene, methanol and combinations thereof.

11. A method according to claim 9 wherein said antimicrobial agent is selected from the group consisting of iodine, chlorhexidine, bronopol and triclosan.

12. A method according to claim 9 wherein said antimicrobial agent is an aqueous solution of iodine which comprises polyvinylpyrrolidone-iodine; or elemental iodine and iodide salts; or elemental iodine, hydriodic acid and a surfactant.

13. A method according to claim 9 wherein said antimicrobial agent is an aqueous solution of chlorhexidine which comprises 50% to 99% by weight of water and 1.0 to 50% by weight of chlorhexidine salts.

14. A method according to claim 9 wherein said polyurethane is derived from an aromatic polyisocyanate and a polyether polyol; or is derived from an aliphatic polyisocyanate and a polyether polyol; or is derived from an aromatic polyisocyanate and a polyester polyol; or is derived from an aliphatic polyisocyanate and a polyester polyol.

15. A method according to claim 9 wherein the poly(N-vinyl lactam) is a water-soluble polyvinylpyrrolidone homopolymer; or is a poly(N-vinyl caprolactam) homopolymer.

16. A method according to claim 9 containing at least one additional polymer component which is compatible therewith.

17. A method according to claim 16 wherein said additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

18. A method according to claim 9 further including at least one agent selected from the group consisting of skin conditioning agents, colorants, fragrances and insect repellants.

19. A method according to claim 18 wherein said skin conditioning agent is selected from the group consisting of glycerin, glycols, polyols, lanolin, aloe vera and vitamins.

20. A method according to claim 9 wherein said composition further comprises a thickener selected from the group consisting of a silica and xanthan gum.

* * * * *